(12) United States Patent
Thuemen

(10) Patent No.: US 11,751,752 B2
(45) Date of Patent: Sep. 12, 2023

(54) VIDEO ENDOSCOPE

(71) Applicant: OLYMPUS WINTER & IBE GMBH, Hamburg (DE)

(72) Inventor: Alrun Thuemen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 122 days.

(21) Appl. No.: 17/368,201

(22) Filed: Jul. 6, 2021

(65) Prior Publication Data

US 2022/0007922 A1 Jan. 13, 2022

(30) Foreign Application Priority Data

Jul. 10, 2020 (DE) .......................... 102020118264.3

(51) Int. Cl.
*A61B 1/00* (2006.01)
*G02B 23/24* (2006.01)
*A61B 1/07* (2006.01)

(52) U.S. Cl.
CPC ...... *A61B 1/00124* (2013.01); *A61B 1/00114* (2013.01); *A61B 1/00117* (2013.01); *A61B 1/07* (2013.01); *G02B 23/2492* (2013.01)

(58) Field of Classification Search
CPC ............ A61B 1/00124; A61B 1/00114; A61B 1/00117; A61B 1/07; A61B 1/00121; A61B 1/00126; G02B 23/2492; G02B 23/2476
USPC ...................................................... 600/132
See application file for complete search history.

(56) References Cited

U.S. PATENT DOCUMENTS

| 4,697,870 | A | * | 10/1987 | Richards | .............. | G02B 6/3888 |
| | | | | | | 385/125 |
| 5,810,620 | A | * | 9/1998 | Kobayashi | ......... | A61B 1/00128 |
| | | | | | | 439/607.17 |
| 5,876,326 | A | * | 3/1999 | Takamura | .......... | H01R 13/6581 |
| | | | | | | 600/110 |

(Continued)

FOREIGN PATENT DOCUMENTS

| AT | 521108 A2 | 10/2019 | | |
| DE | 19925323 A1 | 12/2000 | | |
| DE | 102016112801 A1 | * 1/2018 | ......... | A61B 1/00126 |

(Continued)

OTHER PUBLICATIONS

German OA dated Apr. 16, 2021 issued in DE 102020118264.3.

*Primary Examiner* — Aaron B Fairchild
(74) *Attorney, Agent, or Firm* — Scully, Scott, Murphy & Presser, P.C.

(57) ABSTRACT

A video endoscope including an elongated shaft, a main body, a cable for conducting control signals, video signals and/or illumination light, wherein the cable includes: a core having an optical fiber bundle, a video signal line, and/or a control signal line; a mechanical protective layer; and a sheath tube; a junction body sealingly inserted into the main body on to sealingly receive the sheath tube; an anti-kink sleeve disposed around the sheath tube to engage over the junction body, a clamping ring supported on the junction body pulled towards the main body by a first clamping nut presses the junction body against a round cord seal between the junction body and the main body and presses the anti-kink sleeve against the junction body such to seal a cavity between the anti-kink sleeve and the junction body.

10 Claims, 2 Drawing Sheets

(56) References Cited

U.S. PATENT DOCUMENTS

2001/0025135 A1* 9/2001 Naito .................. A61B 1/015
600/156
2021/0098932 A1 4/2021 Zechmann

FOREIGN PATENT DOCUMENTS

DE 102019100136 A1 7/2020
GB 2352922 A * 2/2001 ......... A61B 1/00126
GB 2352922 A 2/2001

* cited by examiner

VIDEO ENDOSCOPE

CROSS-REFERENCE TO RELATED APPLICATION

The present application is based upon and claims the benefit of priority from DE 10 2020 118 264.3 filed on Jul. 10, 2020, the entire contents of which is incorporated herein by reference.

BACKGROUND

Field

The present disclosure relates to a video endoscope and more particularly to a video endoscope having an elongated shaft, a main body disposed proximally of the shaft, and a cable fixedly connected to the main body for conducting control signals, video signals and/or illumination light to and/or from the video endoscope, wherein the cable comprises: a core, comprising at least one optical fiber bundle, at least one video signal line, and/or at least one control signal line; a mechanical protective layer surrounding the core; and a sheath tube surrounding the protective layer; wherein the video endoscope further comprises a junction body, which is sealingly inserted into the main body on the endoscope side, and which sealingly receives the sheath tube on the cable side; and wherein an anti-kink sleeve is disposed around the sheath tube in the region of the cable connection and engages over the junction body.

Prior Art

Video endoscopes have long been used in medicine to examine cavities in a patient's body that are difficult to access. For this purpose, video endoscopes have an elongated shaft that is inserted through a natural or surgically created orifice into the body cavity to be examined. The shaft can be flexible or rigid, depending on the intended application. An objective lens is arranged at a distal end of the shaft, with which a structure of interest in the body cavity to be examined can be imaged. An image generated by the objective lens is imaged onto an electronic image converter, which generates video signals representing the image.

To illuminate the body cavity to be examined, optical fibers are usually installed in the shaft of a video endoscope, which emit light coupled at a proximal end of the video endoscope in a directed manner at its distal end.

For the output of the video signals, for the input and output of further control signals and/or for the supply of illumination light, modern video endoscopes are equipped with a permanently mounted cable. The cable is permanently mounted on the video endoscope to avoid hard-to-clean detachable connections in the application close to the patient. At an end of the cable remote from the video endoscope, one or more connectors are disposed to detachably connect the cable to a control unit and/or to a light source. These connectors can be made larger and are therefore less problematic to clean than connectors directly placed on the video endoscope.

Special sealing standards are required for the connection point of the cable to the video endoscope. On the one hand, the connection must be configured so that no moisture can enter the interior of the video endoscope during use and reprocessing. Sufficient sealing is essential, especially for reprocessing in an autoclave with steam under increased pressure. On the other hand, the connection must not have any leakage through which contaminated liquids or soiling can intrude into areas that are difficult to access.

Furthermore, the connection should be configured in such a way that assembly and/or disassembly is as uncomplicated as possible.

These requirements in combination are only incompletely fulfilled in known video endoscopes.

SUMMARY

It is therefore an object to provide a video endoscope which is improved with respect to the sealing and the mountability of the cable connection.

Such object can be achieved by a video endoscope comprising an elongated shaft, a main body disposed proximally of the shaft, and a cable fixedly connected to the main body for conducting control signals, video signals, and/or illumination light to and/or from the video endoscope, wherein the cable comprises: a core, comprising at least one optical fiber bundle, at least one video signal line, and/or at least one control signal line; a mechanical protective layer surrounding the core; and a sheath tube surrounding the protective layer; wherein the video endoscope further comprises a junction body which is sealingly inserted into the main body on the endoscope side and which sealingly receives the sheath tube on the cable side; and wherein an anti-kink sleeve is disposed around the sheath tube in the region of the cable connection and engages over the junction body; which is further configured in that the video endoscope further comprises a clamping ring which is supported on the junction body and is pulled in the direction of the main body by a first clamping nut so that the junction body is pressed against a round cord seal disposed between the junction body and the main body and which at the same time presses the anti-kink sleeve against the junction body in such a way that a cavity formed between the anti-kink sleeve and the junction body is sealed off from the interior of the main body and from the environment.

Due to such configuration, a single element, namely the clamping ring, can be used to seal both the main body and an end area of the anti-kink sleeve in a simple manner. For this purpose, only the first clamping nut may be tightened.

The main body may comprise an external thread on the cable side, onto which the first clamping nut is screwed.

The materials of the first clamping nut, the clamping ring and the anti-kink sleeve may be selected such that a friction coefficient of the material pairing of the first clamping nut and the clamping ring is lower than a friction coefficient of the material pairing of the clamping ring and the anti-kink sleeve. This ensures that the clamping ring does not twist on the anti-kink sleeve while the first clamping nut is tightened. Damage to the anti-kink sleeve by the clamping ring is thus avoided.

The clamping ring and the first clamping nut may have complementary radial stop surfaces. Such stop surfaces allow the first clamping nut to be easily tightened without causing the clamping ring to tilt or cant.

The junction body may comprise a first partial body and a second partial body, wherein the first partial body sealingly receives the sheath tube, and the second partial body is pressed against the round cord seal. In this case, a largest outer diameter of the first partial body may be smaller than a smallest inner diameter of the main body.

By appropriately configuring the junction body, the main body can slide over the cable past the first part body after removing the second part body to reach components inside the main body.

The main body may engage over the first partial body, and the round cord seal may be disposed between the main body and the first partial body in such a way that it is radially sealingly applied to the main body and to the first partial body by the compressive force of the second partial body.

The first partial body and the second partial body may be screwed together by a thread.

The first partial body may comprise a second clamping nut which compresses an elastic sealing element disposed between the first partial body and the sheath tube. Again, compression of the sealing element in the axial direction may cause radial expansion of the sealing element so that it sealingly contacts the sheath tube and the first partial body.

The clamping ring may press the anti-kink sleeve against the second clamping nut.

BRIEF DESCRIPTION OF THE DRAWINGS

The embodiments are explained in more detail below with reference to a number of exemplary drawings, the embodiments shown being intended solely to provide a better understanding of the invention without limiting it, in which.

DETAILED DESCRIPTION

Figure 1:
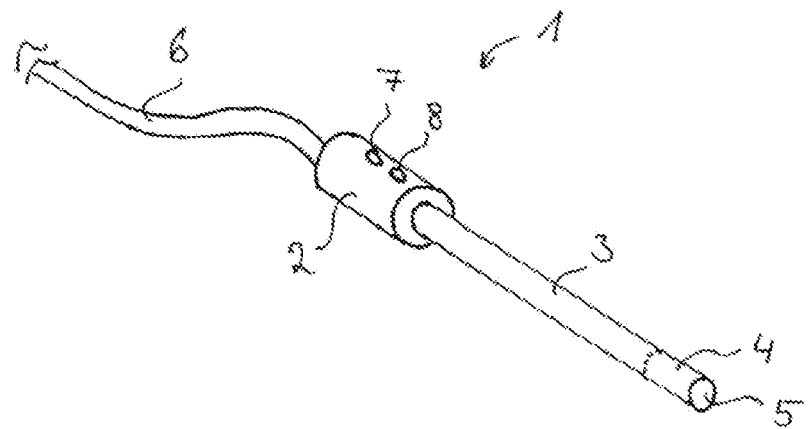
FIG. 1 illustrates a video endoscope.

FIG. 1 shows a video endoscope 1 with a main body 2 and an elongated shaft 3. In the distal portion of the shaft 3 an objective lens 4 and an electronic image converter not shown are disposed. The shaft 3 is closed at the distal end by a window 5.

A supply and signal cable 6 is used to connect the video endoscope 1 to a light source not shown and to a control unit also not shown. Finger switches 7, 8 are provided on the main body 2 of the video endoscope 1, by which the video endoscope 1 and, if necessary, the light source and/or the control unit may be controlled.

Figure 2:
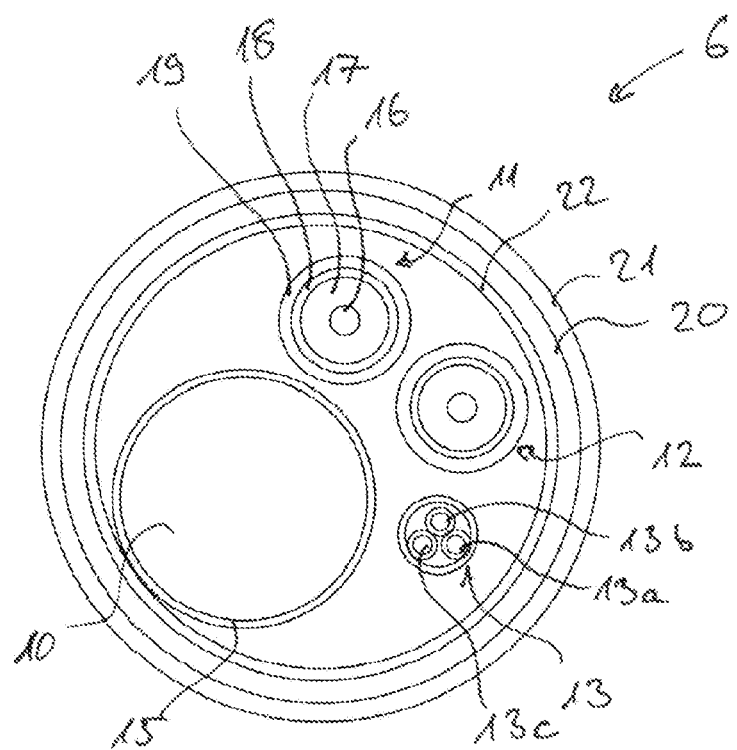
FIG. 2 illustrates a cable.

FIG. 2 shows the structure of the cable 6 in cross-section. The cable 6 comprises a core, which includes an optical fiber bundle 10, video signal lines 11, 12, and a signal line 13.

The optical fiber bundle 10 is coated with a special protective sleeve 15 to protect the sensitive fibers.

The video signal line 11 is configured as a coaxial cable with an inner conductor 16, a dielectric 17, an outer conductor 18, and a sheath 19. The structure of the video signal line 12 is similar to video signal line 11. The two video signal lines 11, 12 enable transmission of a stereo video signal when the video endoscope 1 is configured as a stereo video endoscope. The cable 6 may also comprise only a single video signal line.

In the example shown, the signal line 13 comprises three individually insulated cores 13a, 13b, 13c within a common sheath. The signal line may be used, for example, to transmit the signals from the finger switches 7, 8.

The core of the cable 6 is enclosed by a mechanical protective layer 20, which may be a steel helix, for example. The protective layer 20 is surrounded by a sheath tube 21, which also provides insulation for the cable 6.

An elastic membrane 22 may be provided on the inside of the protective layer 20 to protect against damage to the core of the cable 6 by the edges of the steel helix.

The arrangement of the components of the core of the cable 6 is shown with greatly enlarged spaces to allow a better view. In fact, the optical fiber bundle 10 and the individual lines 11, 12, 13 are arranged close together in the core of the cable 6 to minimize the cross-section of the cable 6.

Figure 3:
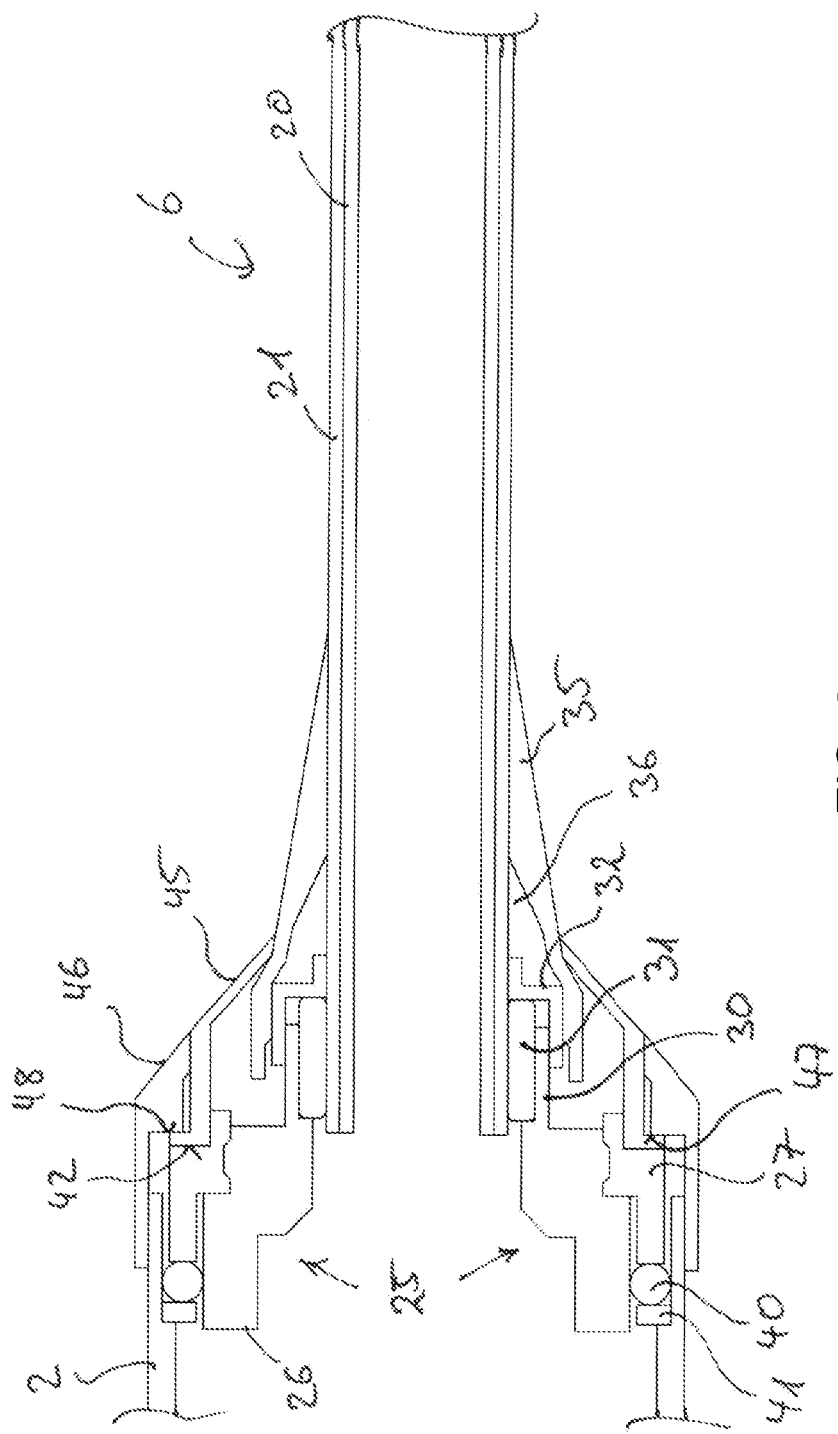
FIG. 3 illustrates the cable connection of a video endoscope.

FIG. 3 shows the cable connection of a video endoscope in longitudinal section. The cable 6 is shown on the right side, wherein for clarity only the mechanical protective layer 20 and the sheath tube 21 are shown. The core of the cable 6 is not shown. On the right side, the main body 2 is shown.

Between the main body 2 and the cable 6 a junction body 25 is shown, which consists of a first partial body 26 and a second partial body 27.

The first partial body 26 has a tubular extension 30 on the cable side, which engages over the endoscope side end of the cable 6. An elastic sealing element 31 is disposed between the extension 30 and the cable 6, which is axially tensioned by a clamping nut 32 screwed onto the extension 30. The sealing element 31 expands radially and thus forms a seal between the sheath tube 21 and the extension 30.

To improve the effectiveness of the sealing element 31, the sheath tube may be supported from the inside at its end on the endoscope side by a sleeve not shown. The sleeve may be arranged between the protective layer 20 and the sheath tube 21 or within the protective layer 20.

The cable connection further comprises an anti-kink sleeve 35 which fits tightly on the sheath tube 21 and engages over the extension 30 of the junction body 25.

For sealing the junction body 25 against the main body 2, a round cord seal 40 is provided, which contacts a support ring 41 on the endoscope side and the main body 2 on the outside. The support ring 41 serves to provide a sufficiently large contact surface for the round cord seal 40.

On the inside, the round cord seal 40 contacts the first partial body 26 of the junction body 25, and on the cable side, the second partial body 27 of the junction body 25 contacts the round cord seal 40.

On the cable side, the second partial body 26 has a radial stop surface 42 which is in contact with a clamping ring 45. The clamping ring 45 is screwed onto the main body 2 with a clamping nut 46. For this purpose, the main body 2 comprises an external thread which is not shown.

The clamping nut 46 and the clamping ring 45 have complementary radial stop surfaces 47, 48.

By tightening the clamping nut 46, the clamping ring 45 is pulled in the direction of the main body 2. In the process, the second partial body 27 presses against the round cord seal 40 so that the latter expands radially and, in the process, sealingly contacts the first partial body 26 and the main body 2. This reliably protects the inside of the main body 2 against the intrusion of moisture from the outside.

At the same time, the cable-side end of the clamping ring 45 presses against the anti-kink sleeve 35 so that it is pulled tightly against the first partial body 26 or against the clamping nut 32. As a result, the cavity 36 is reliably sealed against the intrusion of soiling or germs from the outside.

In order to prevent twisting of the clamping ring 45 when the clamping nut 46 is tightened, the materials of the clamping ring 45, the clamping nut 46 and the anti-kink sleeve 35 are selected such that a friction coefficient of the material pairing of the clamping nut 46 and the clamping ring 45 is significantly lower than a friction coefficient of the material pairing of the clamping ring and the anti-kink sleeve 35. This ensures that the clamping nut 46 slides on the clamping ring 45 so that the latter is only pulled in the axial direction towards the main body 2.

The clamping nut 46 may be made of a thermoplastic material such as PEEK, while the clamping ring 45 itself may be made of metal, for example medical grade stainless steel. The anti-kink sleeve 35 may be made of silicone, for example.

The surface of the clamping ring 45 may be visually and haptically adapted to the needs of a user by having a coating. For example, a coating with tin nitrate can be used to achieve a surface that is resistant to chemicals.

On the cable side, the clamping nut 46 and the clamping ring 45 comprise a conical outer contour. The inner surface of the clamping nut 46 contacts an outer surface of the clamping ring 45 without any gaps as far as possible. The above-mentioned materials make it possible to manufacture the components with correspondingly close tolerances at reasonable cost.

If the interior of the main body 2 needs to be accessed for maintenance or repair purposes, the described cable connection may be easily disassembled. To do this, the clamping nut 46 is loosened and slid to the right over the cable 6. Then the clamping ring can also be slid to the right over the cable 6.

Next, the second partial body 27 is loosened from the first partial body 26 and also pushed to the right over the cable 6. Then the main body 2 itself with the support ring 41 and the round cord seal 41 may be slid over the cable 6 to expose the components to be serviced.

After disassembly of the cable connection, the elastic round cord seal 41 may have to be replaced. To do this, the old round cord seal 41 can be cut to remove it. The new round cord seal, when internal connections of the lines 11, 12, 13 running in the cable 6 and of the optical fiber bundle 10 have been loosened, can be easily slipped over the corresponding connectors and over the first partial body 26. Then, the round cord seal must be passed internally through the support ring 41. After the maintenance has been completed, the cable connection is assembled in reverse order.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A video endoscope comprising:
    an elongated shaft,
    a main body disposed proximally of the shaft,
    a cable fixedly connected to the main body at a junction between a main body side of the main body and a cable side of the cable, the cable being configured to transmit one or more of control signals, video signals and illumination light to and/or from the main body, wherein the cable comprises:
        a core comprising one or more of:
            at least one optical fiber bundle configured to transmit the illumination light to and/or from the main body,
            at least one video signal line configured to transmit the video signals to and/or from the main body, and
            at least one control signal line configured to transmit the control signals to and/or from the main body;
        a mechanical protective layer surrounding the core; and
        a sheath tube surrounding the protective layer;
    a junction body disposed at the main body on the main body side of the junction and disposed at the sheath tube on the cable side of the junction such that the junction body is sealed relative to both the sheath tube and the main body;
    a round cord seal disposed between the junction body and the main body;
    an anti-kink sleeve disposed around the sheath tube in a region of the junction, the anti-kink sleeve being configured to engage over the junction body; and
    a clamping ring supported on the junction body;
    a clamping nut configured to pull the clamping ring in a direction of the main body to press the junction body against the round cord seal disposed between the junction body and the main body and the clamping nut being further configured to press the anti-kink sleeve against the junction body such that a cavity formed between the anti-kink sleeve and the junction body is sealed off from an interior of the main body and from an outside environment.

2. The video endoscope according to claim 1, wherein the main body comprises an external thread on the cable side, the first clamping nut having an internal thread configured to matingly engage with the external thread.

3. The video endoscope according to claim 1, wherein a material of each of the first clamping nut, the clamping ring and the anti-kink sleeve is such that a friction coefficient of a material pairing of the first clamping nut with the clamping ring is lower than a friction coefficient of a material pairing of the clamping ring with the anti-kink sleeve.

4. The video endoscope according to claim 1, wherein the clamping ring and the first clamping nut have complementary radial stop surfaces.

5. The video endoscope according to claim 1, wherein:
    the junction body comprises a first partial body and a second partial body,
    the first partial body being configured to seal relative to the sheath tube, and
    the second partial body is configured to press against the round cord seal.

6. The video endoscope according to claim 5, wherein a largest outer diameter of the first partial body is smaller than a smallest inner diameter of the main body.

7. The video endoscope according to claim 6, wherein the main body is disposed over the first partial body, and the round cord seal is disposed between the main body and the first partial body such that the round cord seal seals the main body relative to the first partial body by the compressive force of the second partial body.

8. The video endoscope according to claim 5, wherein the first partial body and the second partial body having first and second mating threads, respectively, to fix the first partial body to the second partial body.

9. The video endoscope according to claim 5, wherein the first partial body comprises a second clamping nut configured to compress an elastic sealing element disposed between the first partial body and the sheath tube.

10. The video endoscope according to claim 9, wherein the clamping ring is configured to press the anti-kink sleeve against the second clamping nut.

* * * * *